(12) United States Patent
Nita (10) Patent No.: US 7,717,853 B2
(45) Date of Patent: May 18, 2010

(54) METHODS AND APPARATUS FOR INTRACRANIAL ULTRASOUND DELIVERY

(76) Inventor: Henry Nita, 2047 Seabrook Ct., Redwood Shores, CA (US) 94065

(*) Notice: Subject to any disclaimer, the term of this patent is extended or adjusted under 35 U.S.C. 154(b) by 251 days.

(21) Appl. No.: 11/203,738

(22) Filed: Aug. 15, 2005

(65) Prior Publication Data

US 2007/0016041 A1    Jan. 18, 2007

(51) Int. Cl.
*A61B 8/14* (2006.01)
(52) U.S. Cl. .................................. 600/466; 600/467
(58) Field of Classification Search ......... 600/407–480; 601/2–4; 606/128; 604/20–22
See application file for complete search history.

(56) References Cited

U.S. PATENT DOCUMENTS

| | | | |
|---|---|---|---|
| 5,445,155 A * | 8/1995 | Sieben .................... 600/443 |
| 5,620,409 A * | 4/1997 | Venuto et al. .................... 601/2 |
| 5,713,847 A * | 2/1998 | Howard et al. ................ 604/21 |
| 5,927,277 A | 7/1999 | Baudino et al. |
| 5,980,950 A | 11/1999 | Porter |
| 6,019,724 A * | 2/2000 | Gronningsaeter et al. ... 600/439 |
| RE36,939 E | 10/2000 | Tachibana et al. |
| 6,190,323 B1 * | 2/2001 | Dias et al. ................... 600/446 |
| 6,454,757 B1 * | 9/2002 | Nita et al. ................... 604/517 |
| 6,626,902 B1 * | 9/2003 | Kucharczyk et al. .......... 606/41 |
| 6,659,949 B1 * | 12/2003 | Lang et al. .................. 600/438 |
| 6,716,412 B2 | 4/2004 | Unger |
| 7,037,267 B1 * | 5/2006 | Lipson et al. ............... 600/454 |
| 7,517,328 B2 * | 4/2009 | Hoffmann .................... 601/46 |
| 2001/0031243 A1 * | 10/2001 | Unger ........................ 424/9.51 |
| 2002/0062078 A1 * | 5/2002 | Crutchfield et al. ......... 600/453 |
| 2003/0060711 A1 * | 3/2003 | Michaeli ..................... 600/451 |
| 2004/0049134 A1 * | 3/2004 | Tosaya et al. .................. 601/2 |
| 2004/0097996 A1 * | 5/2004 | Rabiner et al. .............. 606/159 |
| 2004/0138562 A1 * | 7/2004 | Makower et al. ............ 600/439 |
| 2004/0138563 A1 * | 7/2004 | Moehring et al. ........... 600/439 |
| 2004/0153009 A1 * | 8/2004 | Horzewski et al. ............. 601/2 |
| 2005/0021013 A1 * | 1/2005 | Visuri et al. .................. 606/15 |
| 2005/0038342 A1 * | 2/2005 | Mozayeni et al. ........... 600/454 |
| 2005/0124897 A1 | 6/2005 | Chopra |
| 2005/0209642 A1 * | 9/2005 | Palti .............................. 607/2 |
| 2005/0215946 A1 * | 9/2005 | Hansmann et al. ............ 604/66 |
| 2006/0058627 A1 * | 3/2006 | Flaherty et al. ............. 600/409 |
| 2006/0079773 A1 * | 4/2006 | Mourad et al. .............. 600/438 |
| 2006/0206028 A1 * | 9/2006 | Lee et al. .................... 600/471 |

* cited by examiner

*Primary Examiner*—Brian Casler
*Assistant Examiner*—Nasir Shahrestani
(74) *Attorney, Agent, or Firm*—Raymond Sun (57) ABSTRACT

A method for delivering ultrasound energy to a patient's intracranial space involves forming at least one hole in the patient's skull, advancing at least one ultrasound delivery device at least partway through the hole(s), and transmitting ultrasound energy from the ultrasound delivery device(s). According to various embodiments, ultrasound delivery devices may be advanced into the epidural space, one or both ventricles and/or an intracerebral space of the patient's brain. In alternative embodiments, one or multiple holes may be formed in the skull, and any number of ultrasound delivery devices may be used. Intracranial ultrasound delivery may be used in diagnostic or therapeutic treatment of ischemic stroke, head trauma, atherosclerosis, perfusion disorders and other acute or chronic neurological conditions.

19 Claims, 4 Drawing Sheets

METHODS AND APPARATUS FOR INTRACRANIAL ULTRASOUND DELIVERY

BACKGROUND OF THE INVENTION

1. Field of the Invention

The present invention relates generally to medical methods and apparatus. More specifically, the invention relates to methods and apparatus for intracranial ultrasound delivery, which may include diagnostic ultrasound, therapeutic ultrasound or both.

Stroke is characterized by the sudden loss of circulation to an area of the brain, resulting in a corresponding loss of neurologic function. Also called cerebrovascular accident or stroke syndrome, stroke is a nonspecific term encompassing a heterogeneous group of pathophysiologic causes, including thrombosis, embolism, and hemorrhage. Strokes currently are classified as either hemorrhagic or ischemic. Acute ischemic stroke refers to strokes caused by thrombosis or embolism and accounts for 80% of all strokes.

More than 400,000 people per year in the U.S. have a first-time stroke. At current trends, this number is projected to increase to one million per year by the year 2050. Stroke is the third leading cause of death and the leading cause of disability in the U.S. Worldwide, cerebrovascular disease was the second leading cause of death in 1990, killing over 4.3 million people. Cerebrovascular disease was also the fifth leading cause of lost productivity, as measured by disability-adjusted life years (DALYs). In 1990, cerebrovascular disease caused 38.5 million DALYs throughout the world. And although stroke often is considered a disease of the elderly, 25% of strokes occur in persons younger than 65 years. When the direct costs (care and treatment) and the indirect costs (lost productivity) of strokes are considered together, strokes cost US society $43.3 billion per year.

Until very recently, almost nothing could be done to help patients with acute stroke. Little treatment existed for ischemic stroke until 1995, when the National Institute of Neurologic Disorders and Stroke (NINDS) recombinant tissue-type plasminogen activator (rt-PA) stroke study group first reported that the early administration of rt-PA benefited some carefully selected patients with acute ischemic stroke. Encouraged by this breakthrough study and the subsequent approval of t-PA for use in acute ischemic stroke by the U.S. Food and Drug Administration, administration of t-PA has become increasingly more prevalent in stroke treatment. Treating patients early enough in the course of stroke, however, is an extremely challenging hurdle to effective treatment of stroke. Furthermore, t-PA for stroke treatment is much more effective if delivered locally at the site of blood vessel blockage, but such delivery requires a great deal of skill and training, which only a small handful of medical professionals possess.

One proposed enhancement for treatment of stroke is the administration of trans-cranial Doppler (TCD) at high frequencies (i.e., approximately 2 MHz) and low intensities, which is normally used for diagnostic functions. TCD has been shown not only to be effective in visualizing clots, but also to be effective in lysing clots in the middle cerebral arteries, in combination with lytic drugs such as t-PA and/or microbubbles. TCD has also been shown to be safe, with no clinically significant brain bleeding effects. (See, for example: A. V. Alexandrov et al., "Ultrasound-Enhanced Thrombolysis for Acute Ischemic Stroke," *N. Engl. J. Med.* 351; 21, Nov. 18, 2004; and W. C. Culp and T. C McCowan, "Ultrasound Augmented Thrombolysis," *Current Medical Imaging Reviews*, 2005, 1, 5-12.) The primary challenge in using TCD to enhance stroke treatment, however, is that the skull attenuates the ultrasound signal to such a high degree that it is very difficult to deliver high-frequency, low-intensity signals through the skull. Using higher intensity ultrasound signals, in an attempt to better penetrate the skull, often causes unwanted bleeding of small intracranial blood vessels and/or heating and sometimes burning of the scalp. The only other option is to carefully aim a high-frequency, low-intensity TCD signal through a small window in the temporal bone of the skull to arrive at the middle cerebral artery, which is the technique described in the studies cited above and is the only technique studied thus far.

There are two main drawbacks to delivering high-frequency TCD through the temporal window. First, such delivery requires a high level of skill, and only a small handful of highly trained ultrasonographers are currently capable of performing this technique. Second, not all intracranial blood vessels are reachable with TCD via the temporal window. For example, although the temporal window approach may work well for addressing the middle cerebral artery, it may not work as well for reaching the anterior cerebral artery or various posterior intracranial arteries.

Assuming effective ultrasound delivery is achieved, in addition to enhancing treatment of acute thrombotic or embolic ischemic stroke, TCD may also enhance and/or facilitate treatment of other cerebral disorders. For example, recurrent lacunar strokes, dementia, head trauma patients with intracerebral blood clots or perfusion abnormalities, and even Alzheimer's patients may benefit from TCD. In any such disorders, administration of TCD may help restore normal blood flow to the brain, help disperse harmful blood clots inside or outside blood vessels, and/or cause hyper-perfusion in one or more areas of the brain, thus enhancing cerebral function. For example, ultrasound administration has been shown to enhance the production of nitric oxide in or nearby blood vessels, which may thus cause vasodilation of nearby arteries and arterioles and enhance tissue perfusion. (See, for example, W. Steffen et al., "Catheter-Delivered High Intensity, Low Frequency Ultrasound Induces Vasodilation in Vivo," *European Heart Journal* (1994) 15, 369-376.) In any such treatments, however, use of TCD faces the same challenges—i.e., it is very difficult to deliver at safe and effective frequencies to desired locations in the brain and thus can be performed only by a small handful of highly skilled technicians and can be directed only to a few areas in the brain. Also, the high intensities required to transmit ultrasound through the skull in TCD make its utility for treating any chronic disorder impractical, since any implantable power source used with a chronic, implantable ultrasound delivery device would be depleted too quickly.

Therefore, it would be desirable to have improved methods and apparatus for intracranial delivery of ultrasound energy for diagnostic ultrasound, therapeutic ultrasound, or both. Ideally, such techniques would be usable by a larger number of medical professionals than are currently qualified to administer TCD. Also ideally, such techniques would use ultrasound frequencies that do not cause unwanted bleeding in other blood vessels in the brain and that do not cause overheating or burning of the skin. At least some of these objectives will be met by the present invention.

2. Background Art

U.S. Pat. No. RE36,939, issued to Tachibana et al., describes the use of microbubbles to enhance the effects of ultrasound delivery, with or without a pharmacological composition. U.S. Pat. No. 6,006,123, issued to Li et al., discloses use of ultrasound energy to enhance bioavailability of pharmaceutical agents. U.S. Pat. No. 5,399,158, issued to Lauer et al., describes a method of lysing thrombi, involving administration of t-PA or other plasminogen activators, with pulsed mode ultrasound. U.S. Pat. No. 6,368,330, issued to Hynes et al., is directed to an apparatus for frameless stereotactic surgery.

BRIEF SUMMARY OF THE INVENTION

In one aspect of the present invention, a method for delivering ultrasound energy to a patient's intracranial space involves forming at least one hole in the patient's skull, advancing at least one ultrasound delivery device at least partway through the hole(s), and transmitting ultrasound energy from the ultrasound delivery device(s). In some embodiments, one hole is placed in the skull, and one ultrasound delivery device is used. In alternative embodiments, multiple holes are formed in the skull, and at least one ultrasound delivery device is advanced at least partway through each hole. In other alternative embodiments, one hole is formed in the skull, and multiple ultrasound delivery devices are advanced through the hole.

The hole (or holes) in the patient's skull may be formed using any suitable devices and methods. For example, in some embodiments a hand or power drill or burr device may be used, such as those commonly known in the art for forming holes in the skull. Once a hole is formed in the skull, one or more ultrasound delivery devices may be advanced partway or completely into the hole or through the hole. In one embodiment, for example, a delivery device is placed into the hole so a distal end of the device is flush with the inner wall of the skull. In other alternative embodiments, one or more delivery devices are advanced through the hole(s) into the epidural space, one or more ventricles and/or an intracerebral space of the patient's brain. For the purposes of this application, "intracerebral space" means any location within brain tissue or parenchyma outside of blood vessels.

To facilitate introduction of ultrasound delivery devices through one or more holes in the patient's skull, one or more introducer devices may optionally be used. For example, in one embodiment an introducer device is placed at least partway into a hole, and at least one ultrasound delivery device is advanced partway or all the way through the introducer device. In one alternative embodiment, the introducer device is advanced through a hole and into the patient's epidural space, and one or more ultrasound devices are thus advanced into the epidural space. In other alternative embodiments, the introducer device may be advanced through the hole and into a ventricle or an intracerebral space of the patient's brain, and one or more ultrasound devices are thus advanced into the ventricle or intracerebral space.

Any suitable ultrasound delivery device may be used in implementing various embodiments of the present invention. For example, in one embodiment, the device may comprise an ultrasound transducer. In another embodiment, the device comprises a transducer-tipped ultrasound catheter. In either case, the ultrasound transducers may be formed from piezoelectric crystal or from silicon-based ultrasonic transducer technology.

In many embodiments, the ultrasound energy is transmitted acutely, such as in treatment of ischemic stroke or acute head trauma. In alternative embodiments, the ultrasound energy may be transmitted chronically, such as in treatment of chronic brain perfusion disorders. In some cases, a device or part of a device may be implanted in the patient for chronic treatment. In various embodiments, any of a number of different conditions may be treated or ameliorated with the methods of the invention. For example, the ultrasound energy may be transmitted to a blood clot, either within or outside of a blood vessel, to help disrupt the clot. In another embodiment, the energy may be transmitted to a blood vessel to treat atherosclerosis of the vessel. In other embodiments, the energy may be transmitted to one or more blood vessels in the brain to help treat any of a number of blood perfusion abnormalities.

Optionally, the method may further include providing one or more pharmacologic agents to the patient, in conjunction with the delivered ultrasound energy. Examples of such agents include, but are not limited to, tissue plasminogen activator and other blood clot reducing agents, such as rTPA, Urokinease, Streptase (Streptokinase) Actiase (Alteplase) and Desmoteplase. Other agents which may be used include antiplatelet agents such as aspirin, Plavix (clopidorgel) and Ticlid (Ticclopidine), and Glib/IIIa inhibitors, such as Reopro (abciximab), Aggrestat (Tirofiban) and Integrilin (eptifibatide). Such a pharmacologic agent may be delivered intravenously, arterially, via intramuscular injection, or orally, in various embodiments. Alternative methods optionally involve delivering microbubbles or nanobubbles into the patient's bloodstream, in conjunction with the delivered ultrasound energy. Such microbubbles or nanobubbles may be delivered intravenously or arterially. In some embodiments, both microbubbles or nanobubbles and a pharmacologic agent may be delivered to the patient along with the ultrasound energy.

Once one or more holes have been formed in the skull, ultrasound energy may be transmitted from any of several locations and in any of a number of different patterns. For example, in one embodiment, multiple holes are formed in the patient's skull, and ultrasound energy is transmitted from multiple delivery devices at multiple locations simultaneously. Such a delivery pattern may be advantageous, for example, in triangulating the ultrasound transmissions toward the same target. In an alternative embodiment, ultrasound energy is delivered sequentially from multiple delivery devices. In some cases, the ultrasound energy is transmitted from multiple delivery devices with the same frequency and intensity. Alternatively, the ultrasound energy may be transmitted from multiple delivery devices with different frequencies, different intensities and/or different modes. Ultrasound energy may be transmitted at any desired frequency, although in preferred embodiments the energy has a frequency between about 10 KHz and about 20 MHz, and more preferably between about 17 KHz and about 10 MHz. According to different embodiments, the ultrasound energy may be transmitted in continuous mode or pulse mode or may be modulated.

At any point during or after advancement of an ultrasound device through a hole in the skull, the location of the device may be monitored via any suitable visualization apparatus. For example, radiographic, computed tomography (CT) or magnetic resonance imaging (MRI) technologies may be used to help facilitate placement of an ultrasound delivery device in a desired location. In some embodiments, radiographs, CT images and/or MRI images may be used before device placement to determine an ideal location for the device. In some embodiments, during ultrasound energy delivery to the target site in the brain, patient recovery status may be monitored using one or more sensing methods, such as but not limited to monitoring of oxygen levels or saturation, rate of carbon dioxide production, heart rate, intracranial pressure and/or blood pressure. Also, the sensing element's measure could be used to modulate the intensity, frequency and/or duty cycle of the ultrasonic device(s). Such a feedback process is also known as a closed loop control system. Some embodiments may also include the use of a disposable patient interface (DPI), a sterile, compliant conductive gel/oil pack which interfaces between the ultrasound transducer and the patient.

In another aspect of the present invention, a method for delivering ultrasound energy from within a patient's epidural space involves advancing at least one ultrasound delivery device through at least one hole in the patient's skull to locate at least a distal portion of the device in the patient's epidural space and transmitting ultrasound energy from the ultrasound delivery device(s). Such a method may further involve forming the hole(s) in the patient's skull. According to various embodiments, any of the features or variations of the methods described above may be implemented.

In another aspect of the present invention, a method for delivering ultrasound energy from within at least one ventricle of a patient's brain involves advancing at least one ultrasound delivery device through at least one hole in the patient's skull to locate at least a distal portion of the device in at least one ventricle of the patient's brain and transmitting ultrasound energy from the ultrasound delivery device(s). Again, such a method may further include forming the hole(s) in the patient's skull. Any of the features or variations described above may be implemented in various embodiments.

In another aspect of the present invention, a method for delivering ultrasound energy from within an intracerebral space of a patient's brain involves advancing at least one ultrasound delivery device through at least one hole in the patient's skull to locate at least a distal portion of the device an intracerebral space of the patient's brain and transmitting ultrasound energy from the ultrasound delivery device(s). The method may further include forming the hole(s) in the patient's skull. And again, any of the features or variations described above may be implemented, according to various embodiments. Delivery of ultrasound energy from the intracerebral space may be used for treatment of any of a number of conditions, such as acute clot outside of blood vessels caused by brain trauma or ischemic stroke caused by a clot within a vessel. In various embodiments, ultrasound may be combined with delivery of a pharmacological agent, microbubbles/nanobubbles or both. Ultrasound, with or without additional agents, may be delivered until the patient's symptoms improve and/or until a brain imaging study (e.g. MR, CT, PET, SPECT) demonstrate that the adverse "mass effects" of a clot outside are significantly reduced (e.g., <10% in size). For treatment of clot inside a vessel, as in ischemic stroke patients, the ultrasound delivery device may be placed near or directly adjacent to the clotted blood vessel.

Further aspects and embodiments of the present invention are described in greater detail below, with reference to the attached drawing figures.

DETAILED DESCRIPTION OF THE INVENTION

Methods and apparatus of the present invention generally involve delivering ultrasound energy to a patient's intracranial space for diagnostic purposes, or therapeutic treatment, or both. The methods involve forming at least one hole in the patient's skull, advancing at least one ultrasound delivery device at least partway through the hole(s), and transmitting ultrasound energy from the ultrasound delivery device(s). In some instances, such as in treatment of ischemic stroke, ultrasound energy is delivered to a target clot in a blood vessel. In other cases, such as in acute head trauma, ultrasound energy may be directed toward an extravascular blood clot in the brain. In other cases, energy may be delivered toward an area of blood vessels to cause vasodilation and thus increased blood flow. Thus, the techniques and apparatus described herein may be used for a number of different applications and treatments and are not limited, for example, to treatment of an isolated intracranial blood clot or even to ischemic stroke therapy.

Figure 1:
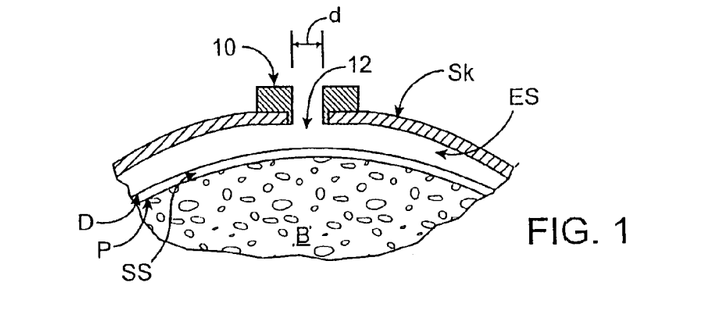
FIG. 1 is a cross-sectional view of a portion of a human skull, showing the skull, brain tissue and epidural space and a hole formed in the skull with an introducer device in place, according to one embodiment of the present invention.

With reference now to FIG. 1, a cross-sectional view of a portion of a human head is shown, with a skull Sk, epidural space ES, dura mater D, subarachnoid space SS, pia mater P and brain tissue B. In various embodiments, one or more holes 12 or openings are formed in the skull Sk using any suitable hole forming device, such as but not limited to a power drill, hand drill, or burr device. In some embodiments, a guide device 10 (or "introducer") is placed in hole 12 to facilitate delivery of one or more ultrasound delivery devices. In alternative embodiments, guide device 10 is not used. Hole(s) and the opening of guide device 10 may have any desired diameters. For example, the opening of guide device 10 may have a diameter d ranging from about 0.5 mm to about 20.0 mm in one embodiment.

Guide device 10 may be attached to the skull Sk by any suitable means. In some embodiments, for example, guide device 10 is pressure fitted within hole 12, while in other embodiments guide device 10 may have threads for screwing into hole 12 or may include a locking mechanism for attaching to the skull Sk. In some embodiments, one or more atraumatic guide catheters (not shown) may be used with guide device 10 to introduce one or more ultrasound delivery devices into hole 12 or into the epidural space ES. Use of such a guide catheter may help ensure that no intracranial structures are damaged.

Figure 2A:
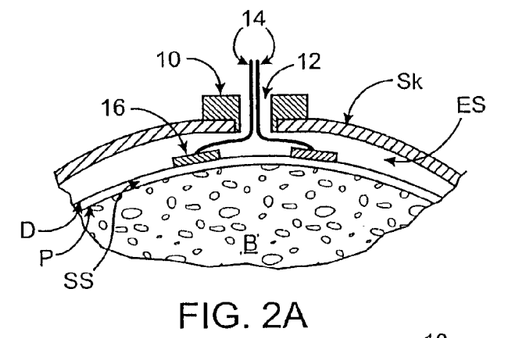
FIG. 2A is a cross-sectional view as in FIG. 1, with multiple ultrasound delivery devices advanced through the introducer device into the epidural space, according to one embodiment of the present invention.
Figure 2B:
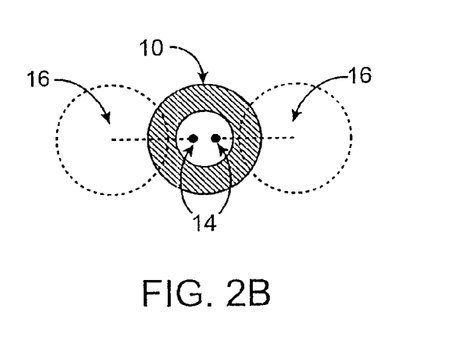
FIG. 2B is a top view of the introducer device and ultrasound delivery devices of FIG. 2A.

Referring now to FIGS. 2A and 2B, in one embodiment, two ultrasound delivery leads 14, each having a transducer 16 (or "ultrasound wand") coupled to its distal end, may be delivered through guide device 10 into the epidural space ES. Transducers 16 may then rest on the dura mater D or float within the epidural space ES, and ultrasound energy may then be transmitted from the wands into the intracranial space. Transducers 16 may be delivered through a microcatheter or via any other suitable delivery technique. Furthermore, any number of ultrasound delivery leads 14 and transducers 16 may be delivered through hole 12, such as from one to ten leads 14 and transducers 16. FIG. 2B shows introducer 10, leads 14 and transducers 16 from a top view.

Figure 2C:
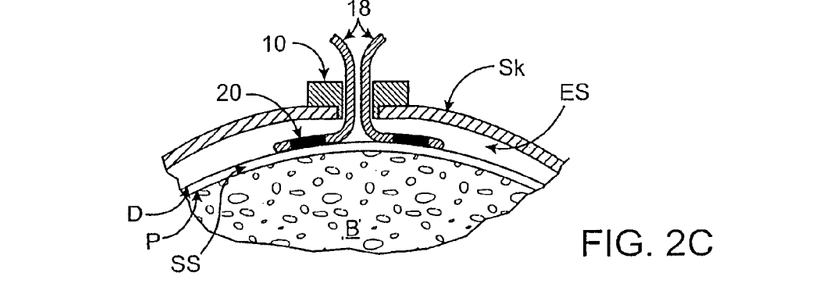
FIG. 2C is a cross-sectional view as in FIG. 1, with multiple catheter-based ultrasound delivery devices advanced through the introducer device into the epidural space, according to an alternative embodiment of the present invention.

Referring now to FIG. 2C, an alternative embodiment is shown in which multiple ultrasound catheters 18 are delivered through hole 12 into the epidural space ES. Each ultrasound catheter 18 includes a distal ultrasound transducer 20, which transmits ultrasound energy into the intracranial space. Again, any number of catheters 18 may be introduced through one hole, such as anywhere from one to ten catheters 18. Catheter 18 may be an over-the-wire or not over-the-wire, in various embodiments. Each catheter 18 may include one ultrasound transducer 20 or may include multiple transducers 20 distributed along its distal portion. In one embodiment, a distal portion of catheter 18 may have a straight configuration when being delivered but may then assume a helical shape when deployed in the epidural space ES, with the helix having a larger diameter than hole 12. The helical portion may then contain multiple transducers to allow transmission of ultrasound in multiple different directions. Catheter 18 also have a deflectable tip to allow it to be moved to various locations within the epidural space ES without causing damage. Transducers 20 may be formed from piezoelectric crystal or using chip technology. In some embodiments, for example, transducers 20 may be fabricated on the surface of a silicon wafer.

Figure 3:
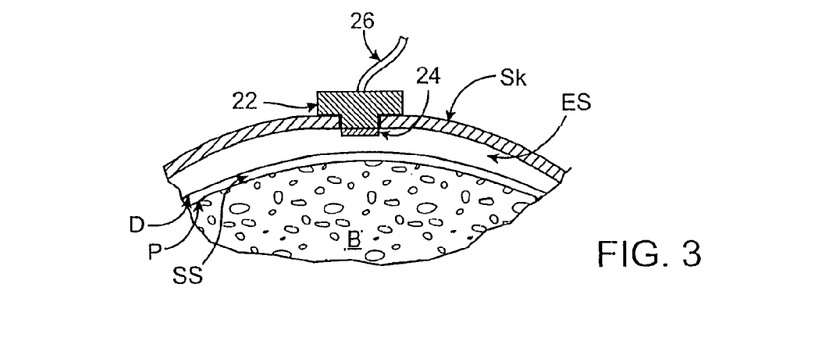
FIG. 3 is a cross-sectional view of a human skull with a hole formed therein and with an ultrasound transducer device in place within the hole, according to an alternative embodiment of the present invention.

With reference now to FIG. 3, in an alternative embodiment, no introducer or guide device is used. Instead, an ultrasound transducer 22 with an ultrasound delivery tip 24 and coupled to a power supply via a lead 26 is placed directly within hole 12 in the skull. Transducer 22 may extend only partway into hole 12 or alternatively may extend all the way into hole 12 or even extend into the epidural space ES, as shown. Transducer 22 is then used to deliver ultrasound energy to the intracranial space.

In any of the embodiments described above, any desired number of holes 12 may be formed in the skull Sk and any desired number of ultrasound delivery devices may be inserted into the holes to deliver ultrasound energy. For example, in some embodiments one hole 12 is formed and one delivery device is used. In another embodiment, one hole 12 may be formed and multiple delivery devices inserted through that hole 12. In other alternative embodiments, multiple holes 12 are formed and either one or multiple delivery devices may be placed through each hole. As described further below, forming multiple holes and using multiple ultrasound delivery devices may be advantageous in some cases in that it allows for the delivery of ultrasound energy from multiple angles simultaneously or in succession.

Figure 4:
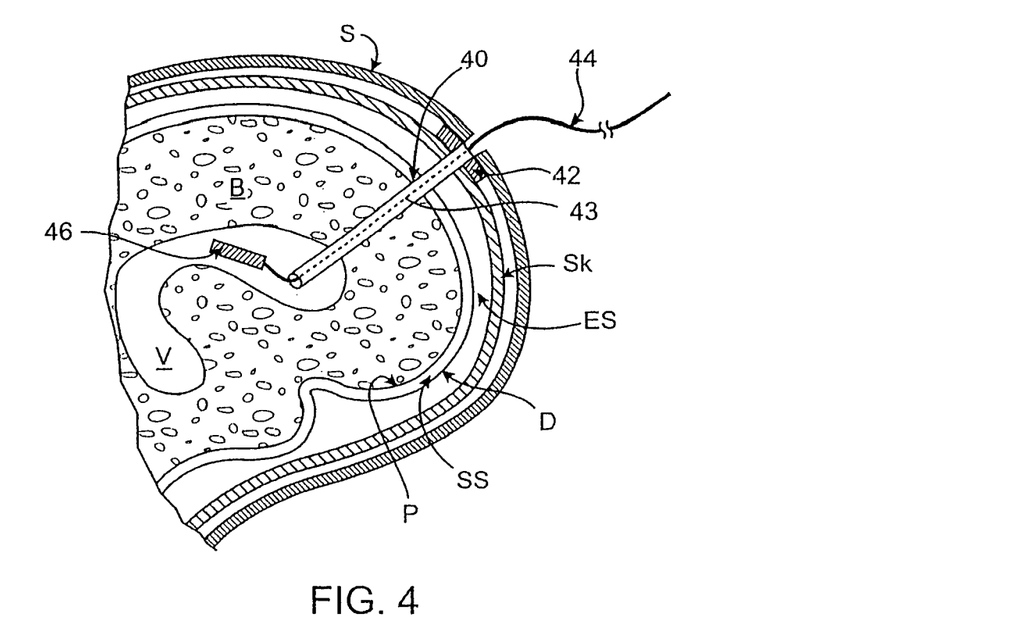
FIG. 4 is a cross-sectional view of a human skull and brain, showing an ultrasound delivery device advanced through a hole in the skull and into a ventricle of the brain, according to one embodiment of the present invention.

Referring to FIG. 4, in some embodiments, a catheter device 40 may be used to advance an ultrasound delivery wand 46 into a ventricle V of a brain B. In one embodiment, catheter 40 includes a hub 42, a catheter shaft 43, a lead 44 and wand 46 attached to the distal end of lead 44. As shown, catheter 40 extends through the scalp S, skull Sk, epidural space ES, dura mater D, subarachnoid space SS, pia mater P and brain tissue B to enter the ventricle V. Hub 42 may rest under the scalp S, as shown, or on top of the scalp S, in various embodiments. Catheter 40 is fully retrievable, so that the wand 46, lead 44, catheter shaft 43 and hub 42 may be easily removed from the patient. Delivering ultrasound energy from within a ventricle V in the brain B may be very advantageous in some cases, depending on the location of the target treatment area.

Figure 5:
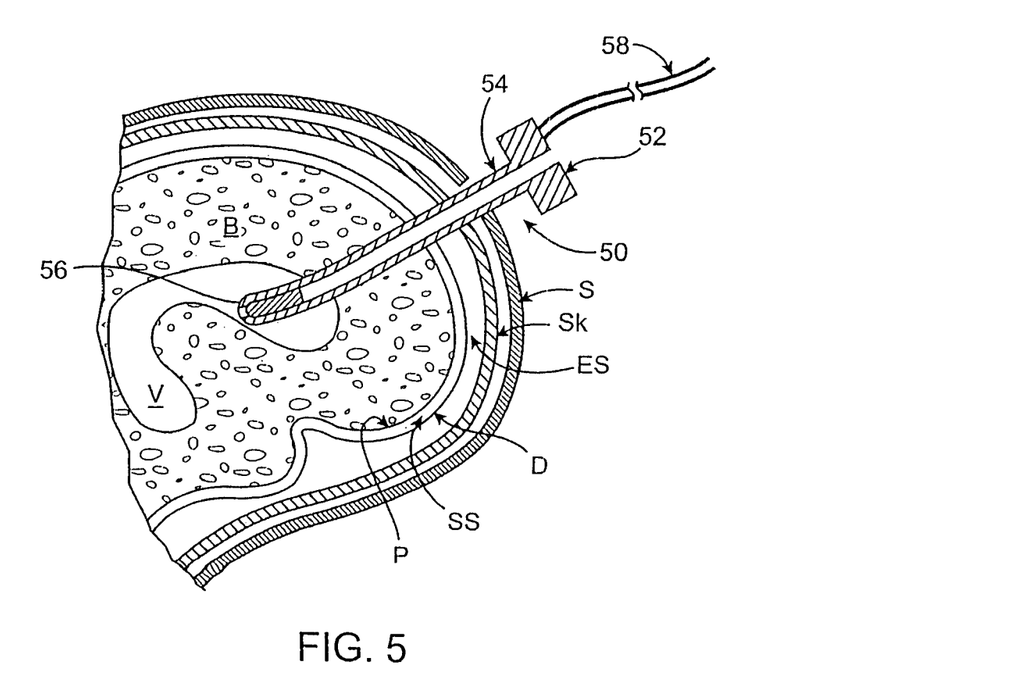
FIG. 5 is a cross-sectional view of a human skull and brain, showing an ultrasound delivery device advanced through a hole in the skull and into a ventricle of the brain, according to an alternative embodiment of the present invention.

With reference now to FIG. 5, an alternative embodiment of an ultrasound delivery device 50 for delivering energy from within a ventricle V is shown. In this embodiment, delivery device 50 includes a hub 52, a catheter shaft 54, a wand 56 at or near the distal end of catheter shaft 54, and a lead 58 coupling device 50 to a power supply. In some embodiments, catheter shaft 54 is steerable, to facilitate delivery of wand 56 into the ventricle V. In various embodiments, hub 52 may reside either outside or inside the scalp S.

In either of the intraventricular approaches just described, or in any other intraventricular approach, the catheter may be placed blindly, via bony landmarks, into one of the ventricles of the brain via a traditional ventriculostomy approach. After forming a hole in the skull, the catheter or guidewire system is placed into the ventricle. When clear cerebrospinal fluid flows out of the proximal end of the catheter, the physician knows the distal end of the catheter is in the ventricle. In an alternative embodiment, intraoperative computed tomography (CT) imaging may be used to help guide placement of the catheter. In another embodiment, preoperative CT and/or MRI scanning may be used with an image-guided system to help guide the catheter into the ventricle. Such image guided systems are provided, for example, by Medtronic, Inc., or BrainLAB, Inc. Once the catheter is placed in the ventricle, one or more transducers may be advanced through the catheter, as in the embodiment shown in FIG. 4. Alternatively, one or more transducers may be included at or near the distal end of the catheter, as in the embodiment shown in FIG. 5.

Figure 6:
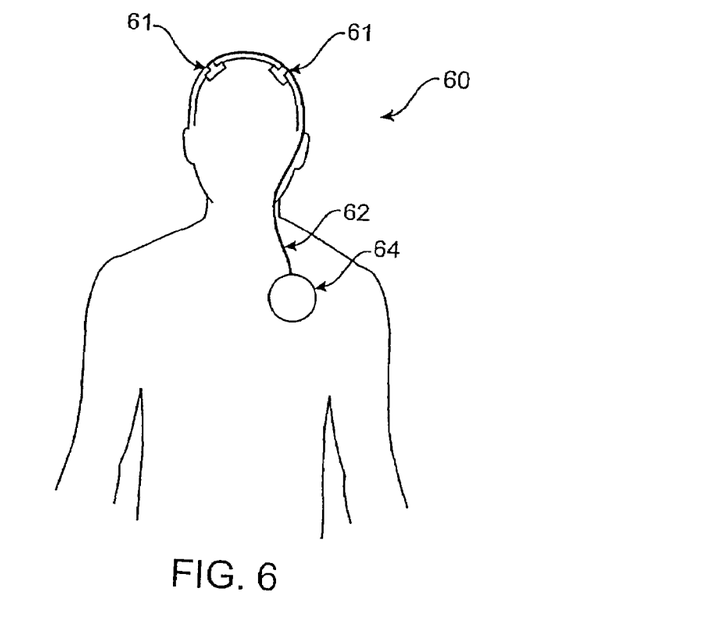
FIG. 6 is a frontal diagrammatic view of a human torso and head, demonstrating an implantable ultrasound delivery system for chronic treatments, according to one embodiment of the present invention.

Referring now to FIG. 6, for some treatments it may be desirable to implant one or more ultrasound delivery devices in a patient and use the devices for chronic therapy. Such implantable devices may be used, for example, in treating Alzheimer's disease or a chronic brain perfusion disorder, or in increasing perfusion over time to enhance brain function. In one embodiment, an implantable ultrasound delivery system 60 includes multiple ultrasound delivery devices 61, coupled with multiple leads 62, which may be tunneled under the scalp and skin to an implanted power source 64 in the chest. In an alternative embodiment, power source 64 may be implanted under the patient's scalp or even inside the patient's skull. One type of intracranial implantable power supply, for example, is provided by Neuro Pace, Inc. Types of implantable power sources include standard lithium ion nonrechargeable or rechargeable batteries. In an another alternative embodiment, the power source 64 could be located external to the body and would transmit the power to an implanted receiver coil in the patient via radio frequency energy. The implantable receiver coil would convert the power into the appropriate form and be connected to the ultrasound system wires. Ultrasound delivery devices 61 may then deliver continuous or intermittent ultrasound energy to one or more intracranial target areas to enhance blood flow. Each device 61 is placed within a hole formed in the skull.

As mentioned above, and with reference now to FIG. 7, in some embodiment multiple ultrasound delivery devices 70 are placed in multiple holes in a patient's skull to deliver ultrasound energy to an intracranial target area from multiple angles. In the embodiment shown, three delivery devices 70a-70c are used to direct energy toward a blockage B in the middle cerebral artery MCA. Triangulation of ultrasound energy signals in this way typically enhances the ability of the energy to break up a blockage B. In embodiments where multiple ultrasound devices 70 are used, energy may be transmitted from devices 70 either simultaneously or at different times. In some embodiments, for example, energy may be transmitted sequentially.

Figure 7:
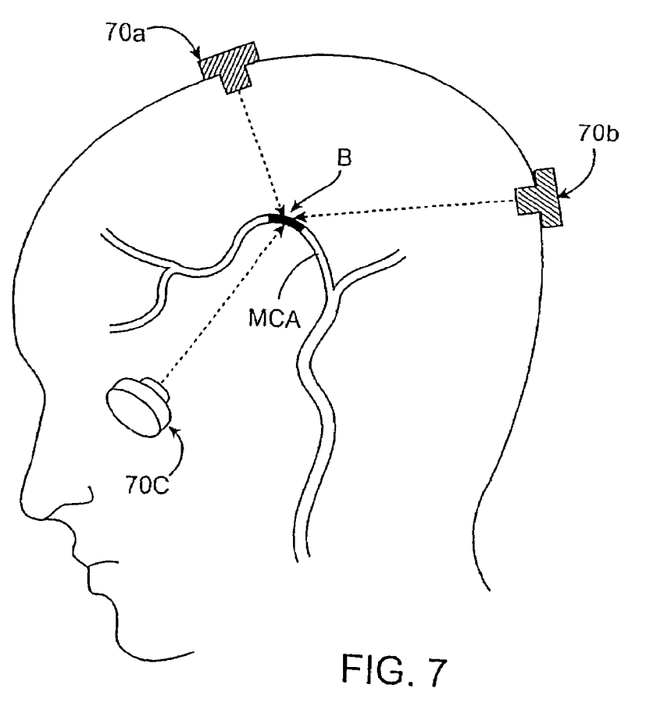
FIG. 7 is a side view of a human head with three ultrasound transducers coupled therewith, demonstrating a triangulation technique for delivering ultrasound energy to a location in the brain, according to one embodiment of the present invention.

In one embodiment of the triangulation method described by FIG. 7, preoperative CT/CTA (computed tomography angiography) and/or MR/MRA (magnetic resonance angiography) images are obtained of the patient's intracranial space. These images are obtained with some type of fiduciaries on the patient's head, such as screw-on or stick-on fiduciaries. Once the images are obtained and a clot location identified, computer software may be used to recommend where to locate the ultrasound delivery devices on the skull or within the epidural space or ventricular space(s). Based on the software recommendations, multiple delivery devices are then placed, typically though not necessarily three or more devices. The ultrasound transducer(s) could be made of MR and/or CT compatible materials so that the related heating or imaging artifacts are minimized during scans. It is important that transducer(s) is made of MR/CT compatible materials because patients with acute stroke may need to be imaged, scanned multiple times to access recovery progress.

In any of the embodiments described above, any desired ultrasound frequency and intensity may be delivered, and ultrasound energy may be delivered in continuous mode, pulsed mode, or a combination thereof. In various embodiments, for example, ultrasound frequencies of between about 20 KHz and about 10 MHz may be used. When pulse mode is used, the pulse mode may vary from about 1% to about 99% of the duty cycle.

Additionally, in various embodiments, ultrasound energy may be delivered along with intravenous or intraarterial drug delivery and/or intravenous delivery of microbubbles or nanobubbles. For example, ultrasound may be delivered along with tissue plasminogen activator and other blood clot reducing agents, such as rTPA, Urokinease, Streptase (Streptokinase) Actiase (Alteplase) and Desmoteplase. Other agents which may be used include antiplatelet agents such as aspirin, Plavix (clopidorgel) and Ticlid (Ticclopidine), and GIIb/IIIa inhibitors, such as Reopro (abciximab), Aggrestat (Tirofiban) and Integrilin (eptifibatide). Microbubbles or nanobubbles of lipids or other suitable substances may also be used.

Once a procedure is completed and the ultrasound delivery device(s) are removed, the hole(s) in the skull may be filled using any suitable technique, such as with known techniques using plugs or bands.

Figure 8:
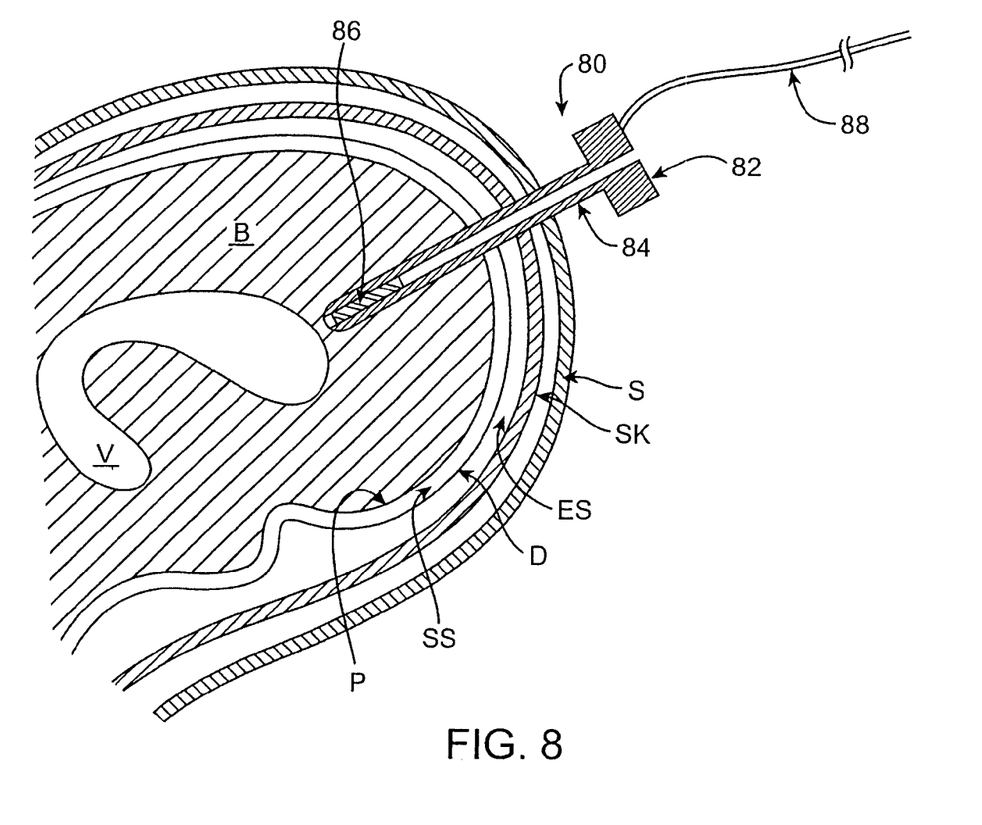
FIG. 8 is a cross-sectional view of a human skull and brain, showing an ultrasound delivery device advanced through a hole in the skull and into an intracerebral space of the brain, according to an alternative embodiment of the present invention.

Referring now to FIG. 8, in some embodiments, a catheter device 80 may be advanced through a hole in a patient's skull Sk so that an ultrasound transducer 86 of device 80 is located in the intracerebral space of the patient's brain B. In one embodiment, catheter device 80 includes a hub 82, a catheter shaft 84, ultrasound transducer 86, and a lead 88 connecting device 80 to a power supply. As shown, catheter device 80 extends through the scalp S, skull Sk, epidural space ES, dura mater D, subarachnoid space SS, and pia mater P and into brain tissue B. Hub 82 may reside outside the scalp S, as shown, or under the scalp S, in various embodiments. Catheter device 80 is fully retrievable. Delivering ultrasound energy from within the intracerebral space in the brain B may be very advantageous in some cases, such as in treatment of acute hemorrhage and/or clot caused by head trauma.

Although the invention has been described fully above, a number of variations and alterations could be made within the scope of the present invention. For example, in alternative embodiments, steps in the various described methods may be carried out in different orders or skipped altogether, and in other embodiments, additional optional steps may be added or one or more steps may be altered. Therefore, the foregoing description of exemplary embodiments should not be interpreted to limit the scope of the invention described by the following claims.

What is claimed is:

1. A method for delivering ultrasound energy to a patient's intracranial space, the method comprising:
   forming at least one hole in the patient's skull to access a target location;
   advancing at least one ultrasound device having a distal portion through the hole, wherein the distal portion contains at least one transducer to allow transmission of ultrasound, and the distal portion can be moved to various locations within the intracranial space without causing damage;
   transmitting ultrasound energy at frequencies between 20 Khz and 10 MHz from the ultrasound delivery device for therapeutic treatment;
   wherein the ultrasound energy is transmitted and directed from outside a blood vessel to a blood clot in the patient's brain at the target location that resides in an intracerebral space of the patient's brain, inside of the blood vessel, to disrupt the blood clot;
   further comprising placing an introducer device into the at least one hole, with the at least one ultrasound delivery device advanced through the introducer device.

2. The method of claim 1, wherein advancing the ultrasound device comprises advancing a device selected from the group consisting of an ultrasound transducer and a transducer-tipped ultrasound catheter.

3. The method of claim 1, wherein the ultrasound energy is transmitted acutely.

4. The method of claim 1, wherein the ultrasound energy is transmitted chronically.

5. The method of claim 1, further comprising delivering at least one pharmacologic agent to the patient.

6. The method of claim 5, wherein the agent is selected from a group consisting of blood clot reducing agents such as tissue plasminogen activator, rTPA, Urokinease, Streptokinase, Alteplase and Desmoteplase, antiplatelet agents such as aspirin, Clopidorgel and Ticciopidine, and GIIb/IIIa inhibitors, such as Abciximab, Tirofiban and Eptifibatide.

7. The method of claim 5, wherein delivering the agent comprises using a method selected from the group consisting of intravenous, arterial and oral delivery.

8. The method of claim 1, further comprising delivering microbubbles or nanobubbles into the patient's bloodstream.

9. The method of claim 8, wherein the microbubbles or nanobubbles are delivered intravenously or arterially.

10. The method of claim 8, further comprising providing at least one pharmacologic agent to the patient.

11. The method of claim 10, wherein the microbubbles or nanobubbles and pharmacological agent are delivered in combination or sequentially.

12. The method of claim 1, further including transmitting the ultrasound energy to a blood vessel in the patient's brain to help treat atherosclerosis of the blood vessel.

13. The method of claim 1, further including transmitting the ultrasound energy to one or more blood vessels in the brain to help treat a blood perfusion abnormality in the patient's brain.

14. The method of claim 1, further providing a conductive medium which interfaces between the ultrasound transducer and the patient.

15. The method of claim 14, further including providing the conductive medium in the form of a compliant pack.

16. The method of claim 15, further providing a gel or oil inside the pack.

17. The method of claim 1, further providing a conductive medium which interfaces between the ultrasound transducer and the patient.

18. The method of claim 1, further including transmitting ultrasound energy for cerebrovascular diagnostics.

19. The method of claim 1, further including transmitting ultrasound energy for cerebrovascular diagnostics and therapeutic treatment.

* * * * *